(12) United States Patent
von Dyck et al.

(10) Patent No.: US 6,595,971 B1
(45) Date of Patent: *Jul. 22, 2003

(54) OSTOMY IRRIGATION SYSTEM

(75) Inventors: Peter M. von Dyck, Fernandina Beach, FL (US); James G. Schneider, St. Louis, MO (US)

(73) Assignee: Zassi Medical Evolutions, Inc., Fernandina Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/362,638

(22) Filed: Jul. 28, 1999

(51) Int. Cl.[7] ................................................. A61F 5/44
(52) U.S. Cl. ...................................................... 604/334
(58) Field of Search ............................ 604/35, 36, 27, 604/28–30, 131, 332, 335–342, 334

(56) References Cited

U.S. PATENT DOCUMENTS

| | | |
|---|---|---|
| 2,139,653 A | 12/1938 | Belfrage |
| 2,494,088 A | 1/1950 | Dulity |
| 3,771,522 A | 11/1973 | Waysilk et al. |
| 4,596,058 A | 6/1986 | Nourbakhsh |
| 4,622,704 A | 11/1986 | Chung |
| 4,637,814 A | 1/1987 | Leiboff |
| 4,655,744 A | 4/1987 | Thistle et al. |
| 4,668,227 A * | 5/1987 | Kay ........................... 604/289 |
| 4,682,979 A | 7/1987 | Girouard |
| 4,804,373 A | 2/1989 | Bloxom, Jr. |
| 4,842,580 A | 6/1989 | Ouelette |
| 4,842,583 A | 6/1989 | Majlessi |
| 4,874,363 A | 10/1989 | Abell |
| 5,019,056 A | 5/1991 | Lee et al. |
| 5,090,067 A | 2/1992 | Cogdill |
| 5,176,697 A | 1/1993 | Hasson et al. |
| 5,190,519 A | 3/1993 | Mead et al. |
| 5,199,945 A | 4/1993 | Chu |
| 5,279,542 A | 1/1994 | Wilk |
| 5,295,274 A | 3/1994 | Daniels et al. |
| 5,330,447 A | 7/1994 | Barth |
| 5,464,391 A * | 11/1995 | DeVale ........................ 604/37 |
| 5,519,900 A | 5/1996 | Gardner |
| 5,527,275 A * | 6/1996 | Ginsberg ....................... 604/38 |
| 5,569,216 A * | 10/1996 | Kim ............................ 604/277 |
| 5,871,463 A | 2/1999 | Baker et al. |
| 6,033,390 A * | 3/2000 | von Dyck ..................... 604/332 |
| 6,106,506 A | 8/2000 | Abell et al. |

* cited by examiner

Primary Examiner—Brian L. Casler
Assistant Examiner—Ann Y Lam
(74) Attorney, Agent, or Firm—Blackwell Sanders Peper Martin LLP

(57) ABSTRACT

An ostomy irrigation system and an ostomy port useful therewith permit independent, hands-free irrigation by a user having an ostomy or surgically created reservoir. The system includes a pump unit capable of providing monitored, controlled pulsations of fluid at a volume and force suitable for safe and convenient introduction into an ostomy of the user; and a reservoir in fluid communication with the pump unit, at least one irrigation connector set including a tube attachable to the pump unit, and a connector nozzle adapted for selectively releasable, substantially fluid tight interlocking connection with an ostomy port in the ostomy of the user so that the system is effectively closed. Controls are also provided for operating the pump unit such that a user of the system can, without the assistance of others, attach the at least one irrigation connector set to the ostomy port in the user's ostomy and, then without further substantial use of the user's hands to control the connector or tubing, introduce irrigation fluid into the ostomy in a controlled and convenient manner.

20 Claims, 11 Drawing Sheets

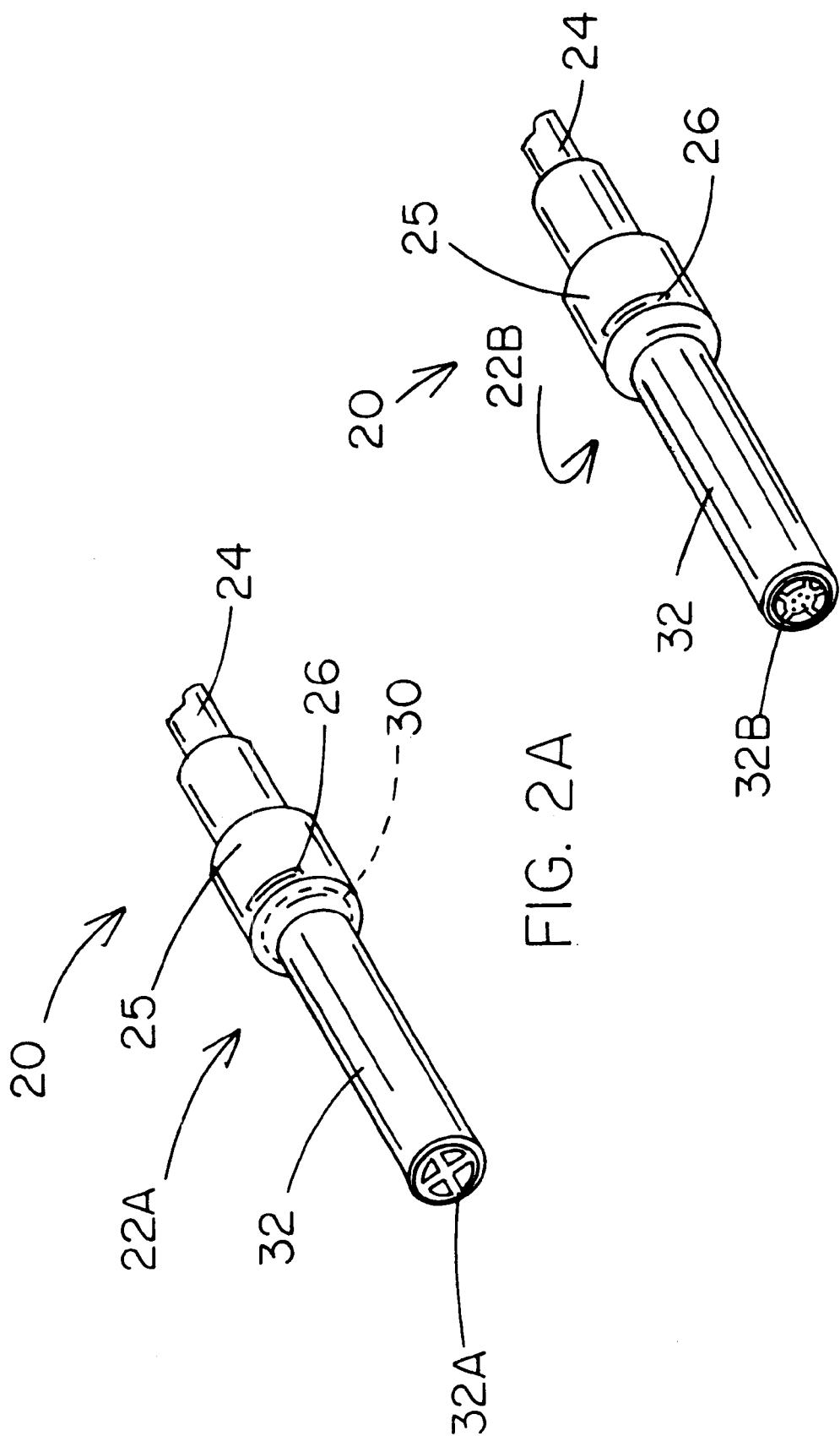

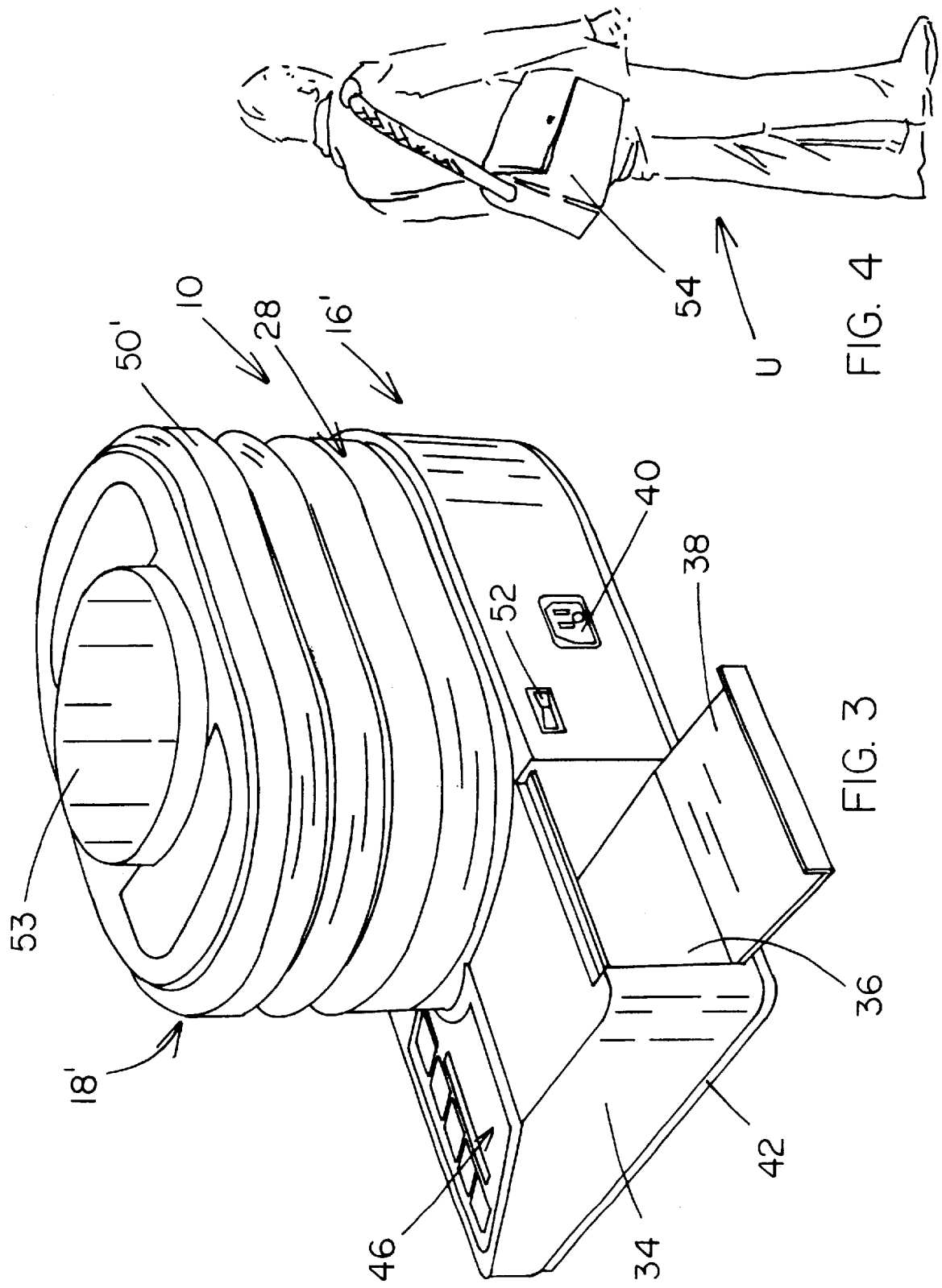

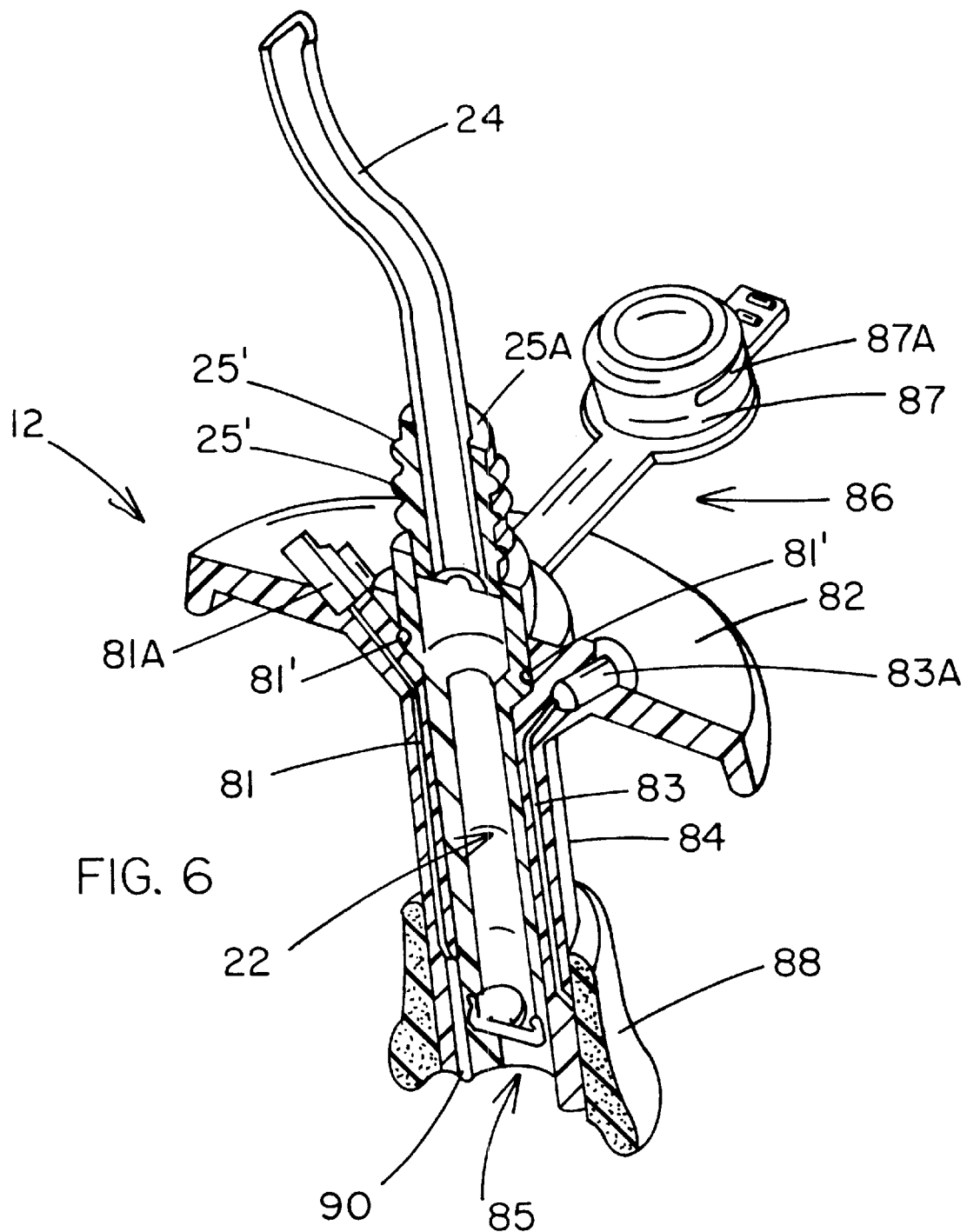

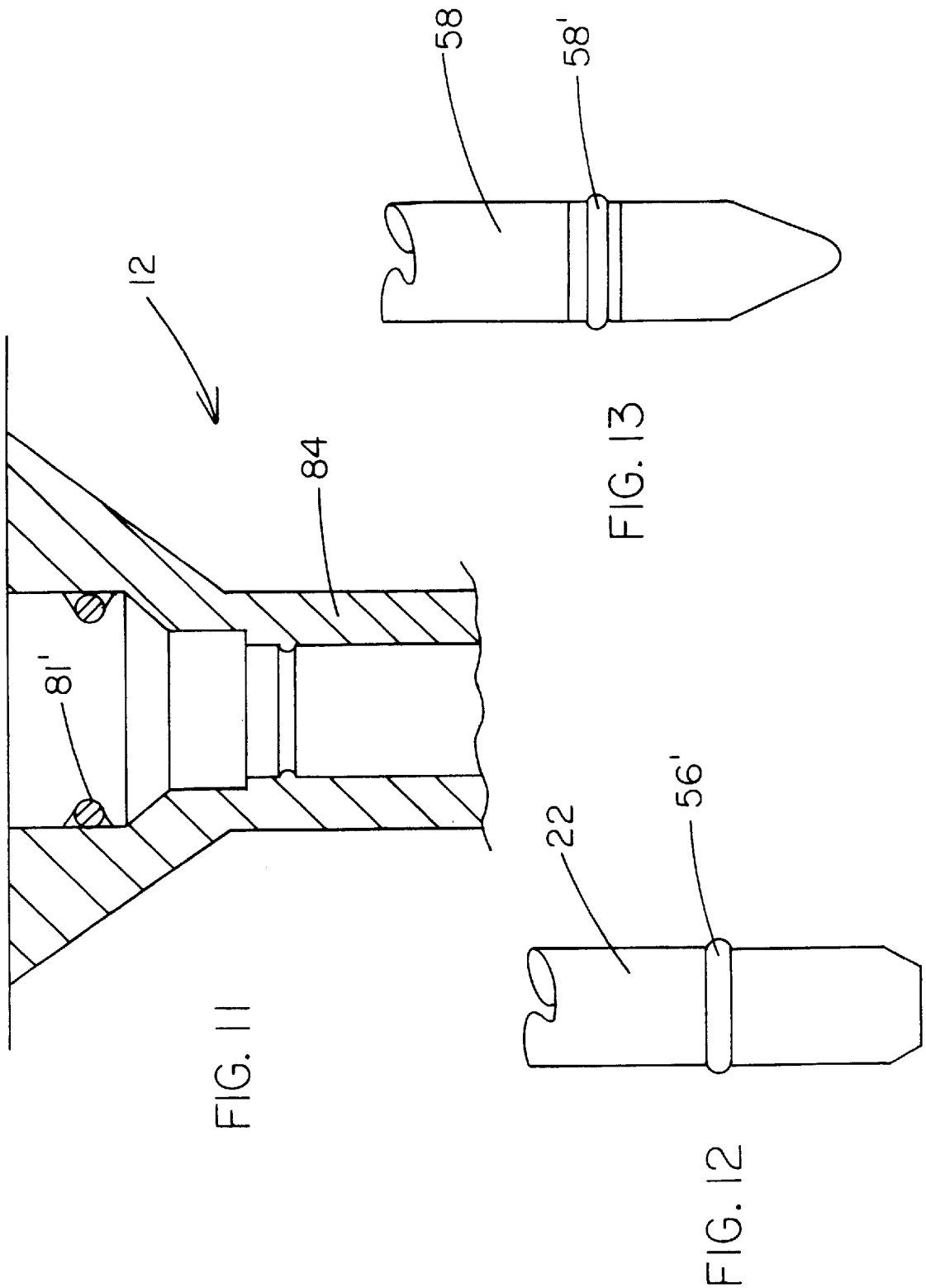

OSTOMY IRRIGATION SYSTEM

BACKGROUND AND SUMMARY OF THE INVENTION

Field of the Invention

The present invention relates to the field of ostomy-related devices, and, more particularly, to a system for use by individuals having a stoma or internal reservoir, including those people having a self-retaining ostomy port of the type described briefly below, and in further detail in our pending related U.S. patent application Ser. No. 09/030,685, which self-retaining continent ostomy port can be inserted into a stoma and secured for long-term placement. The new ostomy irrigation system, having a pulsating pump and specialized adapters, permits hands-free drainage and irrigation of the ostomy, as well as portability and connectability to various types of ports and direct delivery of medicaments or other substances through the stoma site, as well as permitting the user to ambulate between the infusion and evacuation steps of the irrigation process.

BACKGROUND OF THE INVENTION

Surgically formed stomas may be of a variety of types, including, but not limited to, ileostomies, colostomies and urostomies. Although the discussion below will usually describe the invention with reference to the stoma resulting from a colostomy procedure, it is to be understood that the new continent ostomy port can be applied to other types of stomas as well including those interfacing with surgically created internal reservoirs. For simplicity of discussion throughout this document, the term "stoma" will be understood to include stomas emanating from internal reservoir structures as well as normal, intact bowel. Ostomates, individuals who have a stoma, have historically been faced with a variety of problems not ordinarily experienced by the general (non-ostomate) public. Many of these problems are associated with the appliances (i.e. pouches/bags) these individuals are required to wear to manage their surgically created incontinence. These bags surround the outlet to the surgically created stoma and are attached to the individual's abdomen via adhesives, belts or tapes. They provide a container into which fecal matter can continuously drain. Problems associated with these bags include seepage of intestinal gas and waste, such as mucous and liquid and solid fecal material from around the pouch seal. Such seepage not only causes unpleasant and embarrassing odors, but also leads to health and hygiene problems, such as fecal soiling, skin irritation or worse, necrosis of the tissue surrounding the stoma site. This tissue necrosis creates the additional problems of increased expense and increased health risks as a result of the treatment or surgical intervention required to repair the damaged tissue. The bag material can also make bothersome noises during movement as the bag rubs against the user's clothing. For many ostomates, the bulk of the bag beneath clothing also presents a problem. All these negative consequences of having an ostomy can deter social activities of all types, and especially any which are more physical in nature. Frequently, isolation and depression result.

Despite the problems associated with conventional ostomy bags, it is to be understood that the new ostomy ports described herein are capable of accepting an ostomy bag or other accessories adapted to connect to the opening of the new ostomy ports, preferably in detenting and at least substantially leak-proof fashion. Purposes for using a bag with the new ostomy ports include but are not limited to: providing a new user a method of gradually weaning themselves from the use of an ostomy bag and providing a method of temporary collection for a user with a high output ostomy, in instances when they will not be able to get to a toilet facility for an extended period of time.

Additional problems with conventional ostomy systems include allergic reactions to the bag material and/or adhesives used to affix the bag to the abdomen. Both problems can be eliminated by the proposed system which eliminates the long-term need to wear an ostomy bag. It is conceivable, however, that the ostomy ports described herein which are intended primarily to be used without adhesives, could in fact be used with an adhesive, particularly if the new ports are made and used without the preferred internal retention bolster or other structure for maintaining the port in normal operative position.

The known commercial art has made a variety of attempts to address these problems, without clinical success. Although the majority of ostomates use bags to manage body wastes, a number of barrier devices have been developed which essentially completely plug or occlude the stoma until the user is ready to evacuate. Total occlusion of the colon results in a number of problems including the build-up of gases resulting in abdominal cramping, leakage around the device, extrusion of the device from the ostomy and pressure necrosis of the intrastomal intestinal tissue. These occlusive devices, for the most part, have not been clinically viable and many have required revisionary surgery in order to function properly. By contrast, the new continent ostomy port which can be placed in existing stomas without surgical intervention addresses all of these problems. The new continent ostomy port continually filters and vents intestinal gas, while preventing the escape of fecal matter. It has a "bioresponsive" internal retention bolster that adjusts to changes in intracolonic pressure to simultaneously prevent leakage, tissue necrosis and device extrusion.

Many of these previously attempted and presently marketed barrier devices required the device to be completely removed from the stoma in order for the individual to purge (evacuate) and/or irrigate the bowel. The new continent ostomy port permits quick and facile access for irrigating and/or purging the ostomy without removing the port from the stoma or internal reservoir. These necessary procedures, irrigation and purging, as will be made clear hereafter, are made easier and more convenient by use of the system of the present invention.

Because of limitations of the presently marketed ostomy irrigation sets (i.e. a gravity bag with an attached tubing set that terminates in a conical adapter that interfaces with the stoma), some of the shortcomings of the conventional ostomy irrigation process are the time consuming nature of the process (60–90 min.), the confinement of the user to one place (i.e. the user cannot ambulate) during the process and the requirement that the user hold the cone in place during the infusion portion of the process. Water temperature problems also exist with known systems, as discussed further hereafter.

SUMMARY OF THE INVENTION

The new ostomy irrigation system, particularly when used with the described ostomy port, facilitates long-term port access and helps to eliminate the need to continuously wear an ostomy bag and/or the need for cumbersome and lengthy daily irrigation procedures. The long-term access port, described briefly herein (and more completely described and shown in our copending U.S. patent application entitled, Continent Ostomy Port, the specification of which is incorporated herein by reference, in its entirety), prevents leakage sometimes associated with the use of known colostomy management methods because the connection between the new ostomy management system and the user is via this new locking, sealing port which mates internally with the stoma. By contrast, known ostomy management systems conventionally are affixed directly to the stoma site by adhesives or belts, thus permitting leakage because a complete seal at the site of device user interface is not always possible.

The ostomy irrigation system of the present invention is adapted for convenient and facile use in both of the above situations, whether the ostomate is using a conventional ostomy appliance or the new continent ostomy port. The new port device is adapted to be selectively connected to a pouch or tube, as may be necessary from time to time to dispose of waste and to irrigate the intestine for cleanliness and health, while also being capable of being tightly capped for substantial periods of time, even hours, for example, to permit the user to be continent and to have sufficient control to be free to engage in normal physical activities and to function in a wide variety of social settings without fear of leakage and/or embarrassment.

When it is necessary, for ostomates with an ileostomy or wetter colostomies, to void body wastes, simply plugging in a drainage tube adapted to mate with the new port is all that is necessary in the new system for the user to eliminate body wastes directly into a toilet. The tube and connector can easily be carried discretely in a small pouch and cleansed by rinsing with soapy water after use. Such drainage tube and connector are optional elements, which can be included in the new irrigation system or provided separately, and which can be reusable and/or disposable. For ostomates with drier colostomies the new system can be used by pumping fluid into the bowel via a specialized port, trapping the fluid by closing the port, waiting, while either ambulating or resting for a period of time and then draining the bowel contents via a drain tube and adapter described hereafter.

The new system for ostomy/reservoir drainage and automated pumping irrigation is especially beneficial for those ostomates who wish to regulate their bowel evacuation and irrigate their colon instead of wearing an appliance (e.g., ostomy bag) for extended periods of time. The pulsating water delivered by the irrigation pump of the present invention stimulates peristalsis and assists in breaking up and loosening impacted fecal matter, thus dramatically reducing the time required to irrigate an ostomy, as compared to conventional gravity-fed irrigation processes which "chain" the user to an unsightly I.V. pole and restrict the ostomate from ambulating during the irrigation process. A further limitation of gravity irrigation systems is their lack of thrust which greatly slows the irrigation process. By contrast, the new system provides programmable-pressurized bursts of pre-warmed irrigation fluid into the bowel to introduce fluid, as well as to stimulate peristalsis. Although the pulsatile fluid delivery of the new system optimizes the irrigation process, it is to be understood that the new ostomy ports described herein are capable of connecting to a "conventional" gravity set or bag by use of a connector designed to interlock with the opening of the port(s), such as in the manner shown for the drainage tubes and irrigation connectors described further herein.

Yet another limitation of conventional gravity irrigation systems is that they allow the irrigation water (or other fluid) to become uncomfortably cool during the irrigation process, as they provide no adaptation by which to alter or maintain the fluid temperature during irrigation infusion. In addition to being uncomfortable, overly cool irrigation fluid is generally considered to be less effective in loosening stool. This shortcoming, over time, ultimately contributes to lengthening the entire irrigation procedure, which is ordinarily reported to take as long as 60 to 90 minutes.

Aesthetically speaking, ostomates often do not like the "hospital-look" or clutter of an I.V. pole and irrigation bag in the home, because it serves as a reminder of his or her disorder or disease to friends, family and the ostomate of his or her disorder. Such clinical and cosmetic issues, combined with the long infusion times associated with gravity irrigation systems, have deterred many ostomates from adopting irrigation as an option. As a result, ostomates who may be candidates for using existing barrier devices and eliminating the need for a collection bag, frequently choose to continually wear a collection bag rather than spending up to 90 minutes a day irrigating and evacuating.

The irrigation system of the present invention includes a pump mechanism, which will provide prewarmed irrigation fluid in pressurized bursts (or pulses) into the ostomy. A variety of nozzles connectable to the pump diffuse the fluid into the intestine to ensure gentle yet vigorous infusion of irrigants to maximize the loosening of stool and stimulation of peristalsis. Bowel evacuation of fecal matter and/or irrigation fluid then requires simply disconnecting the irrigation nozzle and connecting a drainage tube to the new port or to the stoma via a temporary ostomy port described below. The opposite end of the drain tube is then positioned to drain into a toilet bowl.

Those ostomates who are unable or uninterested in using the new continent ostomy port ("COP"), but wish to irrigate with the automated irrigation can make use of a new temporary ostomy port ("TOP") that is connectable with other portions of the new irrigation system. The temporary ostomy port preferably includes a balloon actuated internal retention bolster at its distal tip which allows the port to self retain inside the stoma for a hands-free procedure similar to that performed with the long term continent ostomy port. This new temporary ostomy irrigation port is designed to accommodate the variation in abdominal wall thickness that may occur between ostomates. For example, the distance between the stoma-lock balloon and anchoring cone resting on the stoma outside the ostomy can be quickly and easily adjusted by screwing the cone portion down or up the shaft of the port device.

Another feature of the temporary ostomy port is that a substantially liquid-tight cap and anti-reflux valve permit the user to disconnect from the pump portion of the system in order to ambulate or engage in other activities while maintaining the irrigation fluids within the bowel for additional dissolution of the impacted fecal matter. Irrigation connectors and drainage tubes both fit the temporary ostomy port and continent ostomy port interchangeably, for convenience and for manufacturing economies of scale. Similarly, gravity bag connectors and conventional ostomy bags can be adapted to interconnect with the ports of the new system. Further, the new irrigation system, including the pump, are easily transported inconspicuously in a carrying case which can have an appearance much like a computer case, brief case or overnight bag. Thus, the various features and construction of the new irrigation system are highly preferable overall, as compared to known gravity fed ostomy irrigation systems.

In addition to simple gravity fed irrigation systems, other known flushing or irrigation devices, such as that described by Lee et al. (U.S. Pat. No. 5,019,056) and Mead et al. (U.S. Pat. No. 5,190,519), include cumbersome equipment which require the user to have assistance and which take up a great deal of space, being designed primarily for institutional use, rather than residential, and which also requires a great deal of water (for example, five gallons) for the purging process. The use of such large volumes of purging water can upset the user's electrolyte balance and potentially cause dehydration or other serious health consequences. In addition, the described features of such known devices necessarily entail a great deal of expense. These costs can be avoided with the new system, which is more than suitable for unassisted home use, as it requires only about one half or two liters of water per treatment and the unit is of a size that makes it easily transportable.

Other known purging devices are more of the bidet type and are not suited for specialized locking (detenting) attachment for hands-free use nor are they specifically designed for the irrigation of colostomies or reservoirs. None of the known irrigation or purging devices offer the flexibility for various uses and types of users, as does the present system.

In addition to the various advantages of the present irrigation system mentioned above, the new system can be used to treat pouchitis (inflammation of the surgically created ileo or anorectal pouches (reservoirs) in ileostomies), by using the pump to vigorously infuse irrigants and thereby breakup the stagnation that contributes to pouchitis. Routine careful use of the system in this manner is expected to reduce occurrence of such inflammations.

Other potential uses for the new pump/irrigation system are: (1) radiological diagnostic procedures, wherein the pump is used to infuse radiological agents prior to x-raying the patient's lower GI tract; (2) treatment for relief of rectal impaction, for which the portable nature of the new system is particularly useful; (3) fluid instillation for enematic purposes; (4) management of incontinence; and (5) to replace gravity bags; i.e., instead of infusing the liquid via gravity through a cone, it can be infused with the new pump system, e.g. through a cone into the stoma or through a new ostomy port. This last procedure may still be of use for certain individuals who desire the pulsation effect, even when the system is used without one of the new ostomy ports. In view of the above, it will be appreciated that a primary advantage of the new ostomy irrigation system, and particularly when used in combination with one of the new ostomy ports, is that there is permitted thereby unique and direct access to the interior of the colon or other stoma site for purposes of diagnosis, observation or treatment.

In view of the various short-comings of the known art, it is among the several goals and advantages of the present invention to provide a system for drainage and irrigation of a stoma, which virtually eliminates leakage of liquid and solid waste from the stoma during drainage and irrigation, and which permits the user to accomplish these time consuming and tedious tasks while still having free use of the user's hands, except for the brief amount of time required for attaching and releasing quick-connect fittings between the ostomy port and the system.

It is further among the advantages of the present system, having the features discussed, that it permits the user to perform the tasks of ostomy drainage and irrigation in much less time than has previously been possible, with very little training and with little to no assistance. The new irrigation system is also: 1) readily portable; 2) controls temperature, pressure and pulse rate and dwell of irrigation fluid with settings that are customized according to the requirements of the individual user; 3) permits disconnection and ambulation during the irrigation process; and 4) requires only a small volume of irrigation fluid, compared to existing pump irrigation systems.

The user of the new system thus is provided with a generally improved quality of life, including enhanced body image, increased confidence and sexuality, and greater freedom of activity. The psychological stress related to concerns with leakage and odor often encountered when an ostomy bag is worn to collect body waste is virtually eliminated with use of the new system. Generally, the present time related deterent that is discouraging those individuals with colostomies who are candidates for irrigation rather than continually wearing a bag have been eliminated.

The previously mentioned, long term continent ostomy port device is adapted for selective use with the new, specially designed drain tubes, and irrigation sets of the system of the present invention. In addition, some individuals have internal surgically created reservoirs, such as those generally known as Kock and Indiana-type pouches, which, similarly, can be drained and irrigated by the new system. The new ostomy irrigation system is also suitable for use with surgically formed urinary and bowel ostomies, as well as with cecostomies, and gastrostomies, and for decompression as well as irrigation and drainage purposes.

The new system described herein is also convenient and surprisingly useful for delivery of strategic agents, such as therapeutic and diagnostic compounds. These may include detection and screening agents, monitory agents or stimulatives, for example. These substances can be introduced directly into the bowel or other ostomy site via the new port by suspending, mixing or dissolving the selected reagent with the irrigation fluid. Such localized delivery permits direct contact with the intestinal tissue, which can be very beneficial, or even required for some substances which would otherwise be altered if taken by mouth and passed through the upper gastrointestinal tract before reaching the desired target in the intestine or urinary system. Thus, medication may be more effective (i.e. because of local rather than systemic delivery) and tests may be performed which would otherwise be painful, difficult or impossible. Also, localized delivery can eliminate some side effects associated with system delivery.

An improved seal and compatibility with irregularly shaped or contoured stomas is readily accomplished with the new long term continent ostomy port ("COP"), as compared with previously known devices for attachment to a stoma. Such improved sealing is seen even with use of the new port device in ostomates who are elderly or obese, or who have soft or flaccid abdomens. Thus, the new irrigation system described herein, which is designed to adapt especially to the new long term port device as well as the new temporary ostomy port device, is designed to also be useful for such individuals with weak, soft or flaccid abdomens, for convenient, hands-free ostomy drainage and irrigation.

The indwelling nature of the new COP also has advantages for use in small children, because the skin is especially sensitive to the adhesives conventionally used for attaching an ostomy bag to an abdomen. In addition, the hands-free operation of the present system is especially useful in the care of small children. When the care giver must necessarily be occupied with otherwise handling the child, it is appreciated that if irrigation is necessary, manipulation of the drainage and irrigation devices of the new system is minimal and highly controllable as far as temperature and pressure.

The indwelling nature of the new COP is also ideal for ostomates who are undergoing skin-grafting or other abdominally located would healing measures, providing reduction in the otherwise high incidences of necrotizing enterocolitis ("NEC") seen in such individuals.

In addition, the indwelling nature of the COP is especially useful in preventing stomal strictures and in improving electrolyte balance in individuals with high output ostomies. The presence of the COP prevents the stoma from collapsing upon itself and the temporary occlusive nature of the COP holds effluent in the ileum longer, thus providing more time for nutrient absorption.

Thus, in furtherance of the above-mentioned goals and advantages, the present invention is, briefly, an ostomy irrigation system which permits independent, hands-free ostomy irrigation by a user having an ostomy or a surgically created reservoir. The system includes a pump unit capable of providing monitored, controlled pulsations of fluid at a volume and pressure suitable for safe and convenient introduction into an ostomy of the user; and a reservoir in fluid communication with the pump unit, at least one irrigation connector set including a tube attachable to the pump unit, and a connector nozzle adapted for selectively releasable, substantially fluid tight interlocking connection with an ostomy port in the ostomy of the user so that the system is effectively closed. Structure is also provided for operating the system such that a user can, without the assistance of others, attach at least one irrigation connector set to the ostomy port in the user's ostomy and the pump unit and, then without further substantial use of the user's hands to control the connector or tubing, introduce irrigation fluid into the ostomy in a controlled, safe and convenient manner.

The invention is also, briefly, a method for irrigating an ostomy using the system of the present invention, and a temporary ostomy port which can be used with the system of the present invention.

These and other advantageous features of the present invention will be in part apparent and in part pointed out herein below.

BRIEF DESCRIPTION OF THE DRAWINGS

FIG. 2A is a perspective view of a connector of the system of FIG. 1, designed to interface the system pump with an ostomy port.

FIG. 2B is a perspective view of an alternate connector of the system of FIG. 1, designed to interface the system pump with an ostomy port.

FIG. 3 is a rear perspective view of an alternative embodiment of the pump unit of the system of FIG. 1, with a cord storage compartment shown open.

FIG. 4 is a schematic illustration of an ostomate user carrying a case for transporting the system of FIG. 1.

FIG. 6 is longitudinal sectional view of the continent ostomy port and irrigation tube of FIG. 5A, enlarged for clarity.

FIG. 11 is schematic, partial longitudinal view of an alternative structure for the distal end of a catheter portion of a continent ostomy port, which is suitable for use with the system of FIG. 1 to drain and cleanse the ostomy in which the port is installed.

FIG. 12 is a schematic partial elevational view of an irrigation connector adapted with tactile position indicator for connection to the continent ostomy port of FIG. 11.

FIG. 13 is a schematic partial elevational view of an obturating cartridge adapted for use with the continent ostomy port of FIG. 11.

Throughout the drawings like parts will be indicated by like element numbers.

DESCRIPTION OF PRACTICAL EMBODIMENTS

Figure 1:
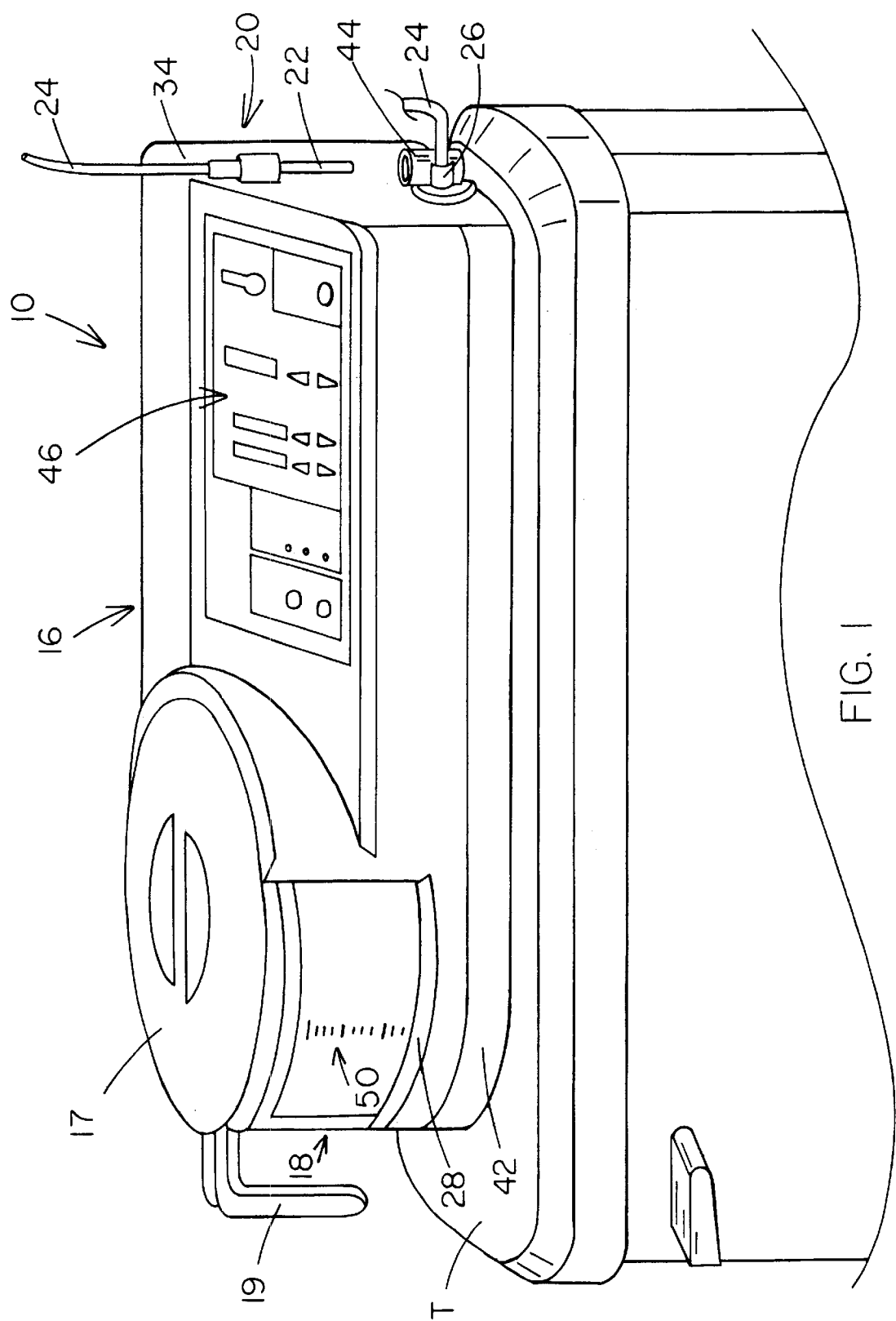
FIG. 1 is a front perspective view, with portions broken away, of a pump unit and an irrigation connector set of an ostomy irrigation system in accordance with the present invention.
Figure 8:
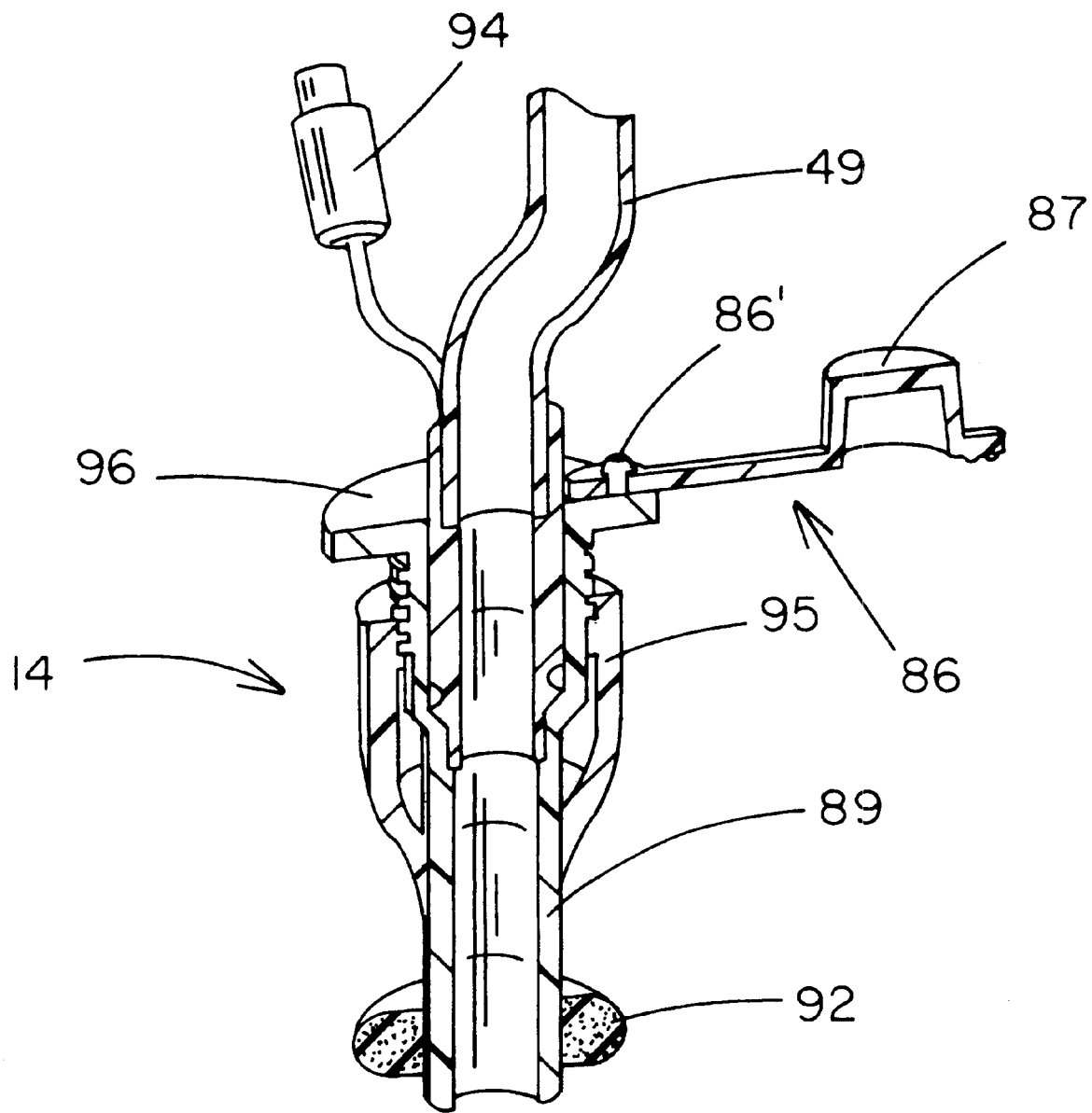
FIG. 8 is a sectional view of a drainage tube of the system attached to a temporary ostomy port for purging of the colon.
Figure 10:
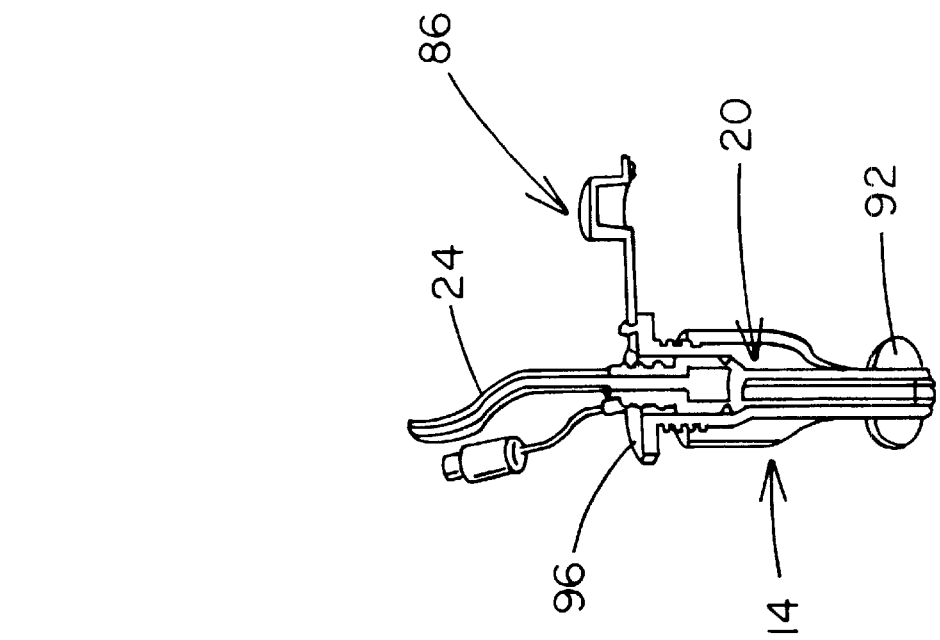
FIG. 10 is a schematic, longitudinal sectional view, reduced, of the temporary ostomy port of FIG. 9 with an irrigation tube connected.
Figure 9:
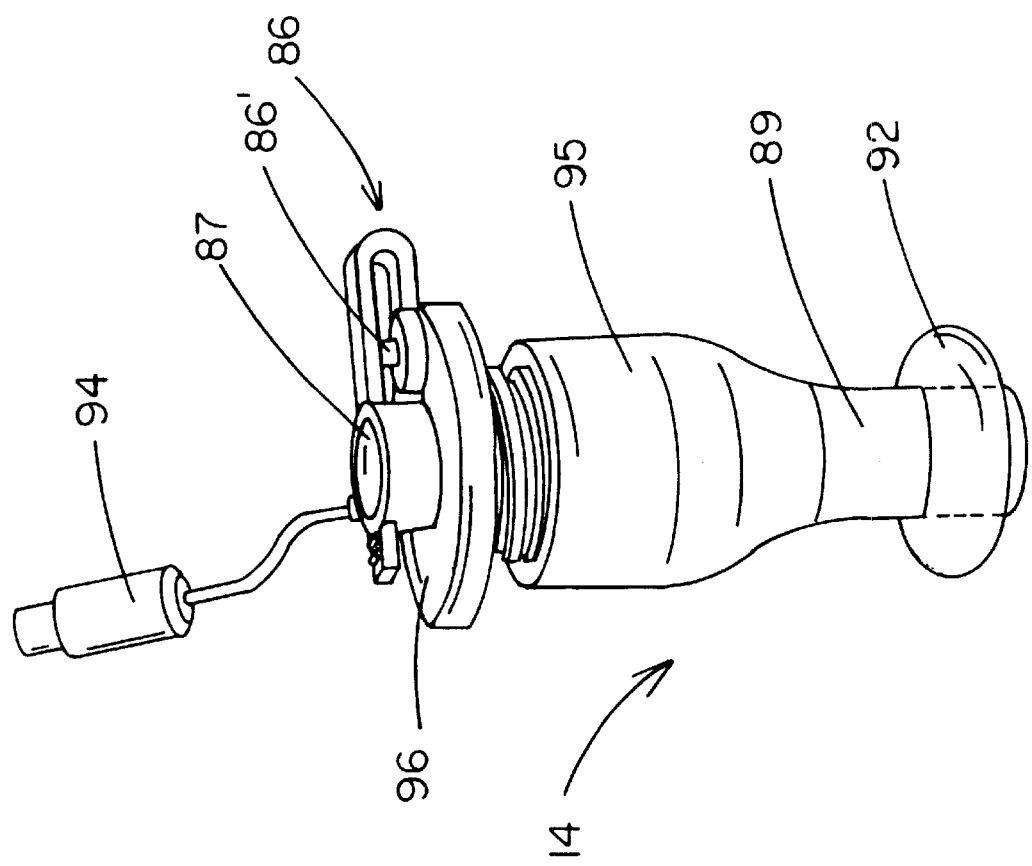
FIG. 9 is a perspective view of the temporary ostomy irrigation port of FIG. 8 in the closed position, is would appear before and after use in combination with the irrigation system.

With reference to the drawings, and particularly FIG. 1, 10 generally designates an ostomy irrigation system constructed in accordance with and embodying the present invention. System 10 is an assembly of specialized parts; including a pump unit, fluid reservoir, tubing, connector sets and appropriate controls, and is intended to be used for irrigating an ostomy of a user. Either an ostomy or internal reservoir of the conventional variety may be treated with new system 10 when used in combination with a temporary ostomy port ("TOP", shown in FIGS. 8–10 and described further hereafter), or with a long-term continent ostomy port device ("COP") of the type previously discussed and exemplified by that shown in FIGS. 5A, 6 and 7, and generally designated 12. COP 12 is described in greater detail in a previously filed application (referenced above) by the owners of the present invention. A temporary ostomy port ("TOP"), generally designated 14 is shown in FIGS. 8, 9 and 10, and is used to connect a pump unit 16 of the system to the stoma of the user in a substantially fluid-tight fashion for performance of bodily irrigation and purging functions in a sanitary and convenient manner.

Constructions of a lesser quality may, however, may be useful and technically fall within the bounds of the present invention. It is further intended that system 10 be manufactured to standards suitable for a shipping environment having a relative humidity in the range of about 20% to about 100%, a temperature in the range of about 0 degrees F to about 120 degrees F, and to be in keeping with any reasonably pertinent government regulations.

The ordinary home or other environment within which system 10 is considered to be useful will have a relative humidity of about 20% to about 100% and a temperature of about 60 degrees F. and about 100 degrees F. It is also intended that the system will be manufactured to such specifications as to be capable of withstanding being bumped or dropped without loss of function or accuracy. It is further expected that the usual environment for the new system will have a relative humidity of about 20% to about 70% and a temperature in the range of about 65 degrees F to about 80 degrees F. Although these conditions are considered ideal, this is not to suggest that the system will be inoperable outside of the preferred operating ranges.

FIG. 1 illustrates that system 10 includes a pump unit, generally designated 16, to which is mounted a fluid reservoir 18 and an irrigation tubing set 20 in fluid communication with reservoir 18 and by which to connect system 10 to an ostomy port, which port will be described hereafter.

Fluid reservoir 18 includes an upstanding side wall which can be straight, and provided with volume indicia, as shown at 50 in FIG. 1, or may be collapsible as shown at 50' in FIG. 3, the alternative. When fluid for irrigation is introduced (e.g., via reservoir opening 53 seen in FIG. 3) into reservoir 18 the control panel 46, as well as the rest of pump unit 16 is maintained in a dry, safe and sanitary condition. Reservoir base 28 is sized and shaped to fit snugly and securely onto housing 34 in known liquid-tight condition, so that water or other irrigation fluid within reservoir 18 can be transferred in controlled manner from the reservoir via irrigation set 20 to the ostomy. Whether the side wall 50' of the reservoir is collapsible or formed as in FIG. 1A, it is sized so that the entire system 10 can be stored and transported within a carrying case 54 such as illustrated in FIG. 4, for easy and inconspicuous portability. If desired, reservoir 18 can have a lid 17 and a handle 19, although neither of these features is critical to the system.

Irrigation set 20 includes a connector nozzle 22 with an anti-reflux valve therein (not seen) disposed to be between the pump and a length of irrigation tubing 24 to prevent backup into the pump. Nozzle 22 is secured to one end of tubing 24, which tubing is preferably of medical grade, but a variety of known sufficiently flexible types are available which will suffice for the present purpose. The opposite end of tubing 24 (proximally disposed in use) is removably attached by a connector 26 to the pump unit 16, for example, as illustrated in FIG. 1.

Irrigation tubing 24 must necessarily be of sufficient length to permit even very tall users to be connected to the pump unit without having to lean or stoop. The diameter of a tubing 24 can vary within a range adequate to permit introduction of a sufficient volume of irrigation fluid at the desired flow rate. The connections at both ends of tubing 24 (to the nozzle and the reservoir) are necessarily liquid tight, and it is also desired that such connections be selectively releasable so that the various elements can be readily removed and cleaned or replaced as necessary.

FIGS. 2A and 2B show, in greater detail than in FIG. 1, two examples of a number of conceivable and acceptable forms for nozzle 22. The particular attachments used will vary with the needs of the user, which needs will in turn vary with the user's own personal anatomy, physiology and diet, for example. Nozzle 22A is considered for use under low pressure, but for providing higher volumes of irrigation fluid, as compared to nozzle 22B, and has a barrel 32 with a tip 32A configured for this application. Nozzle 22B is of a variety conceived for use under high pressure, providing lower volumes of fluid, and having a barrel 32 with tip 32B configured appropriately for such use. Connector nozzles 22A, 22B (or 22, generally) are adapted for liquid-tight, interlocking connection within a collar of the user's ostomy port, whether temporary or long-term.

Figure 5:
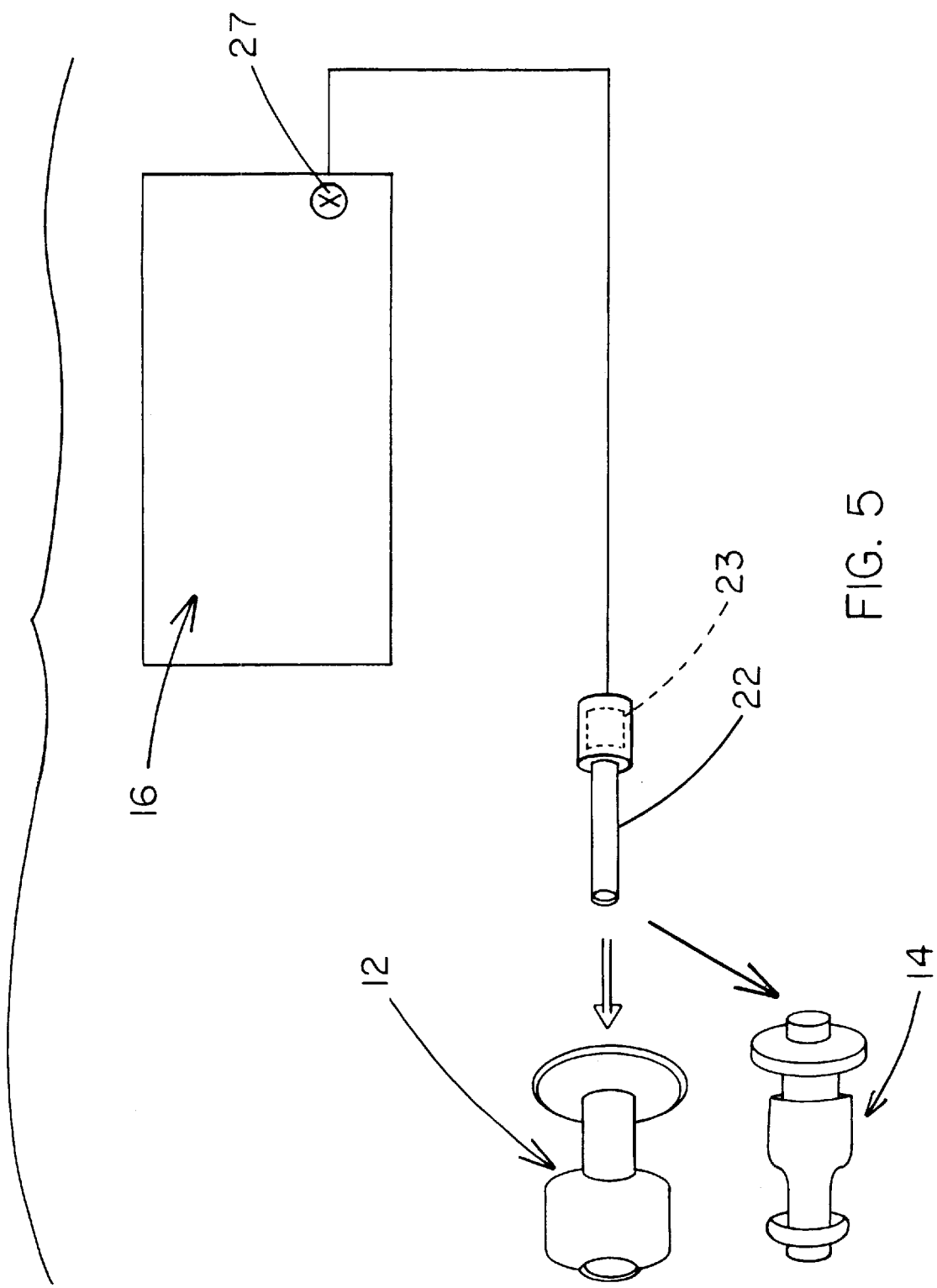
FIG. 5 is a schematic view of the system of the present invention showing the location of a pressure transducer and anti-reflux mechanism ("ARV").
Figure 5A:
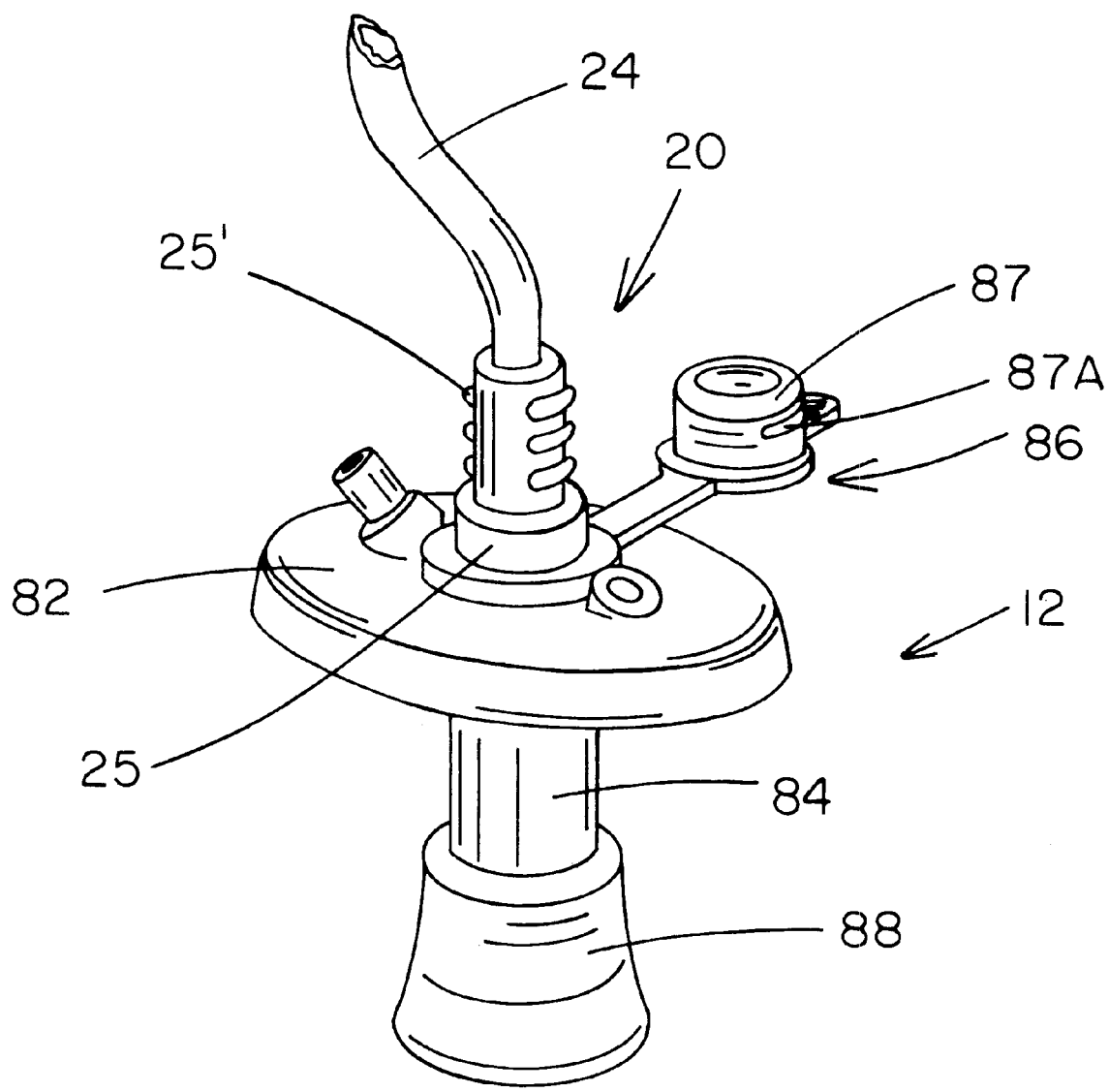
FIG. 5A is a perspective view of one style of a continent ostomy port with an irrigation tube of the system attached, shown partially broken away.

Collar 25 is connected to the irrigation tubing 24 and may optionally include finger grips, such as are indicated at 25', for example, in the version shown in FIGS. 5A and 6. Although not shown in FIG. 7, this feature can also be added to collar 49A of the drainage tube 49. The fit of collar 25 of nozzle 22 into the port is sized and shaped to correspond to the internal shape of the port and is sufficiently snug as to avoid leakage, this sealed fit, along with the sealed fit between the proximal tube connector 26 and the pump 16, provides a "closed" irrigation system. Anti-reflux valve 23 is preferably of known variety and disposed within the nozzle to keep the pump clear, and thereby keep the transducer clear. This closed system is schematically shown in FIG. 5.

If necessary, a gasket 30, shown in broken lines in FIG. 2A, of rubber, silicone or other resilient material can be added on the proximal shoulder of collar 25 to ensure that the connection between the tubing (fluid lines) and the ostomy is liquid-tight. Nozzle 22 preferably includes detent grooves 26 formed in connector collar 25, which grooves engage and retain corresponding detent bars 81' formed inside the collar or neck of the port. An example of this feature is illustrated in section in FIG. 6, with regard to an irrigation set 20, and in FIG. 7 on a drainage tube 49 and the interlocking collar 49A thereof.

With a connector nozzle 22 securely engaged within the port 12 or 14 the user can proceed with the necessary hygienic processes "hands-free"; i.e., without the necessity of holding the drainage/irrigation tube connector in place at the port. Rather, the user's hands are available to do other things, such as shaving, for example, while the irrigation process takes place. Alternatively, depending upon the corresponding detenting mechanism of the particular port in use, the accessory connector nozzles can be provided with a detenting annular ridge or groove(s), to thereby firmly, but selectively releasably, interconnect with the port. This connection could also be a "push and turn" type of connection, or some other known construction, as long as there is a substantially secure, liquid-tight fit between the nozzle and ports 12, 14 and an anti-reflux mechanism (ARV) somewhere between the pump and the port, preferably in the nozzle, for example, as indicated at 23 in FIG. 5. For clarity of the drawings, ARV 23 is not shown in FIGS. 6 or 10.

It is to be understood that nozzles 22A, 22B are examples only and that other irrigation connector set 20 can certainly be conceived that will function satisfactorily, as long as the connection formed is leak proof and selectively releasably lockable, as described with reference to connector nozzles 22A, 22B.

Useful examples of pump unit 16 are illustrated in FIGS. 1 and 3 and, as shown, the pump unit is preferably sized and shaped appropriately to sit stably upon the top of a conventional toilet tank T. It is expected that, ordinarily, that pump unit 16 will have dimensions of approximately seven inches wide, by approximately thirteen inches long, by four inches about high, without fluid reservoir 18 in normal use position. The weight of pump unit 16, again without reservoir 18, is generally between about two to about five pounds. However, it is expected that as new technology and materials are developed the unit may eventually be even smaller and lighter.

Pump unit 16 includes a housing 34 formed of plastic or, conceivably, metal or other suitable material. Housing 34 can optionally be equipped with a handle (not shown) and/or a storage compartment 36 (illustrated in the alternative version shown in FIG. 3), having a door 38, compartment 36 being sized to retain a conventional electric power cord (not shown) which connects at outlet 40 to a standard residential power line. Of course, a heavy-duty adaptation for institutional use is conceivable, if necessary. Housing 34 is mounted on a base member 42, which can be formed at least in part of a non-conductive, slip-proof material, for safety. A holder 44, for example, can be provided on housing 34, to provide a place to rest fluid connector set 20. As shown, the connector set 20 and holder 44 are shown on one side of system 10. However, other positions are conceivable which will be adequate for use and well within the parameters of the invention.

The fluid pump, per se (not seen) is preferably of known medical grade or other conventional variety, compatible with either or both 120 volt, 60 Hz and 220V, 50 Hz power sources, and meets or exceeds minimal safety requirements.

Control panel 46 can take a variety of forms, varying in the selection and arrangement, as well as appearance of the different controls, thus, they are not each specifically indicated in the drawings, but a variety of known, commercially available electronic controls are suitable for the purposes of the present invention. For ease of discussion the individual controls will usually be referred to as "buttons", but will be understood to include any known form of control device, such as knobs, press pads, switches etc., and may include helpful graphics, symbols and even Braille characters, if desired. It is preferred, although not necessarily required, that panel 46 include a power on/off button, a temperature adjust button, a pulsation control, a fluid volume control, a flow rate control, a pressure control, a purge control, and memory controls.

Figure 1A:
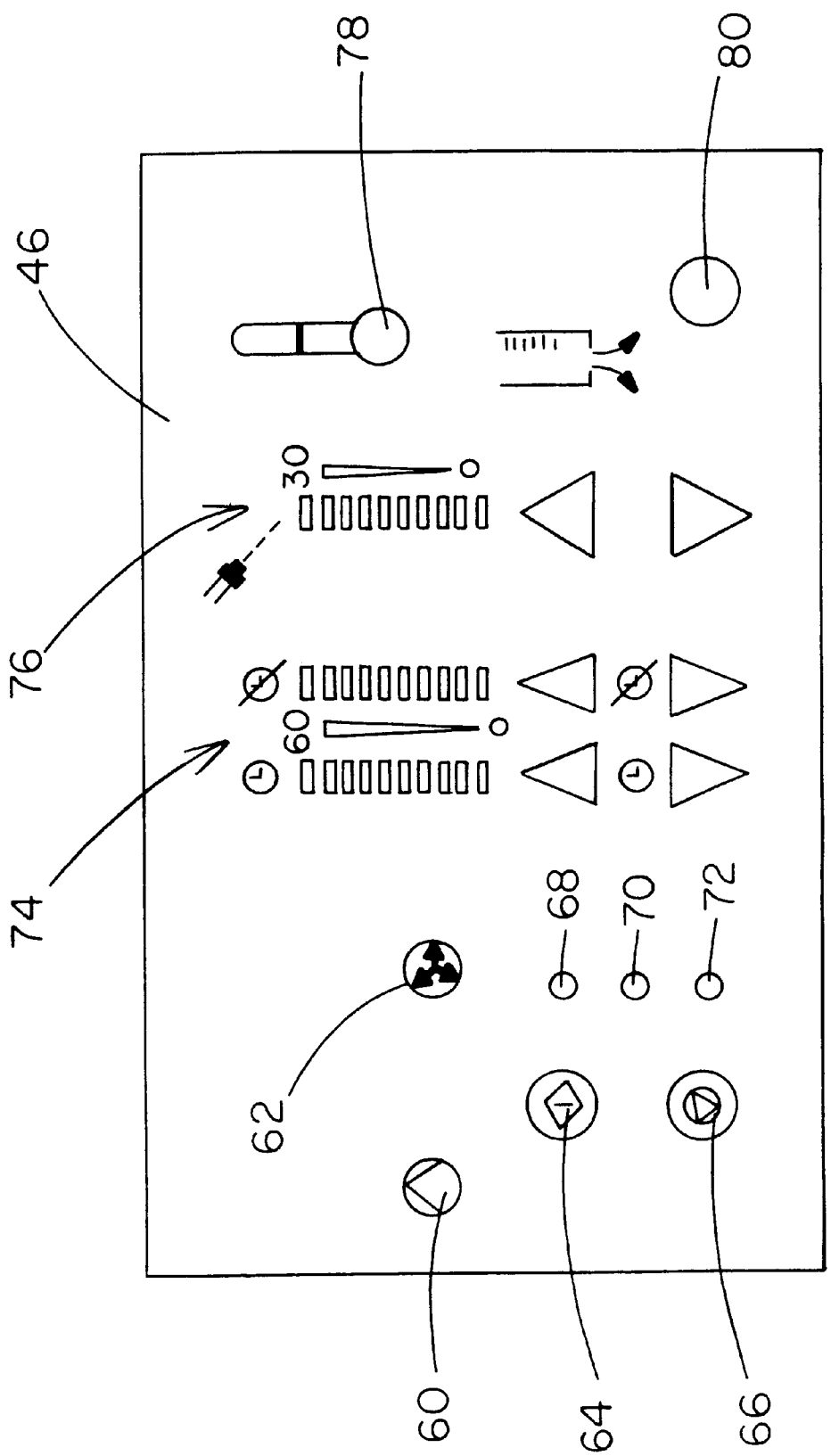
FIG. 1A is a schematic enlarged view of the control panel of the pump unit of FIG. 1.

FIG. 1A schematically illustrates an example of control pad 46 which desirably includes such features as a pump "on" light 60, a pressure "on" light 62, pump start/pause button 64, pump stop button 66, pressure ready, adjusting and shutdown indicators 68, 70 and 72, respectively, a cycle timer 74 with indicators and control buttons for cycle on and off time, a pulse/second indicator 76 with adjustment buttons, a temperature indicator 78 and a purge button 80. It is to be understood that the layout and selection of controls illustrated is presently preferred, but is only one of a number of useful constructions which will be apparent to the artisan.

The sometimes optional, although usually preferred controls available on system 10, are: (1) range of water (irrigation fluid) pulsation; i.e. pulses/second, preferably 0–30-pulses per second in one second increments; (2) adjustment for length of pulsing and non-pulsing intervals, for example, a range of 0–5 minutes, in about 1 second increments, (3) total volume infused, such as about 100 ml to 1500 ml in 10 ml increments; (4) flow rates between about 0.15 liters/minute and approximately 3.0 liters per minute; operating pressure, preferably about one psi, but the pump being capable of producing at least ten psi.; (5) a purge setting, such as a single button on the switch/control panel 46 which, when activated, runs the pump at maximum flow rate in order to flush out the irrigation connector set and tubing thereof after use; (6) a memory to retain previous pump settings (eg. water temperature, pulse rate, length of pulse interval, volume delivered, pre-programmed time-of-day for heater to come on) to be stored when pump is shut-off and recalled when the pump is turned back on for a subsequent use; and (7) water temperature, adjustable in one degree increments from about 96 degrees F. to about 102 degrees F for most normal use, although temperatures outside this range are conceivable for less usual purposes.

The operative state of system 10, including the settings of the controls and the effect of such settings are indicated on a display mechanism such as panel 46 placed for easy viewing on the top or front of housing 34. In the embodiment illustrated in FIG. 1, housing 34 has a top surface that is forwardly and downwardly angled to facilitate the visibility of control panel 46. More specifically, with regard to the display features provided on the new pump unit, some of the desired (although not all being necessarily required) displays are, actual temperature and target temperature; pulsation rate, time of day heater settings and pulse intervals and pressure monitoring, target volume delivered and actual volume delivered, pump running/not running, excessive pressure warning (may be audible), pump status indicators; eg. running, adjusting, shut down. There can also be provided certain warnings/alarms which may be visible and/or audible, such as water too hot/too cold, water level too low in reservoir, excessive back pressure, pump adjusting /shut down, pre-set volume delivered.

It is also preferred that pump unit 16 will not operate if the irrigation connector end 22 is not properly in place, connected to the user's continent ostomy port ("COP") or TOP, as the case may be. The controls of system 10 are, at least in some constructions of the new system, suitable for use by elderly or disabled patients; i.e., readily visible and facile to manipulate and the display/alarm features are designed to be seen and/or heard easily. For example, there can be audible as well as visual feedback by the pump unit either continually, or upon "request" of the unit.

In addition to the preferred controls discussed above, a master power on/off switch 52 is provided, most desirably at a position somewhat separated from the main control panel 46, for example on the back of the pump unit as illustrated in FIG. 3. The intentional distance between the pump switch and the control panel is to help avoid user confusion, to help prevent inadvertent discontinuance of irrigation fluid pumping and to physically isolate the power circuit from the pump controls to improve pump electrical safety.

As an added precaution, as mentioned, it is preferred that pumping cannot be initiated until the irrigation set is firmly connected within the user's ostomy port 12 or stoma irrigation port (TOP) 14. When system 10 is securely connected, to a user's TOP or COP, there is an effectively closed system, as illustrated schematically in FIG. 5. So constructed and used, with an ARV in place, such as indicated in phantom at 23, and a known pressure transducer operatively disposed in line, such as at 27, the closed system is highly efficient and effective for safe and convenient ostomy irrigation. The presence of the pressure transducer permits constant monitoring of the intraluminal pressure during the irrigation process, so as to avoid inadvertent over-pressurizing. If excessive pressure of irrigation fluid is sensed, the control circuit will automatically shut off the pump until the pressure drops to a preselected level, and then will restart the pumping cycle. Of course a variety of useful arrangements of the various controls and displays can be conceived which are within the scope of the present invention, and those illustrated are for purposes of example only.

FIG. 4 is a schematic representation of one example of a carrying case 54 of a style which is useful for holding and transporting system 10. A number of styles for case 54 are considered within the scope of the invention, as long a such case 54 is readily transported by a user U when substantially the entire system 10 is enclosed in the case. Of course case 54 may also be provided with wheels and a retractable handle, as are many currently commercially available suitcases, and other suitable and appropriate modifications to the case will also be apparent to those skilled in the art. Other features desired as part of the present invention are that the system have the "look" of a home appliance, rather than as a medical device, and that it be easy to keep clean, having a water resistant exterior to aid in longevity of system 10, which may occasionally become accidentally splashed during use.

Figure 7:
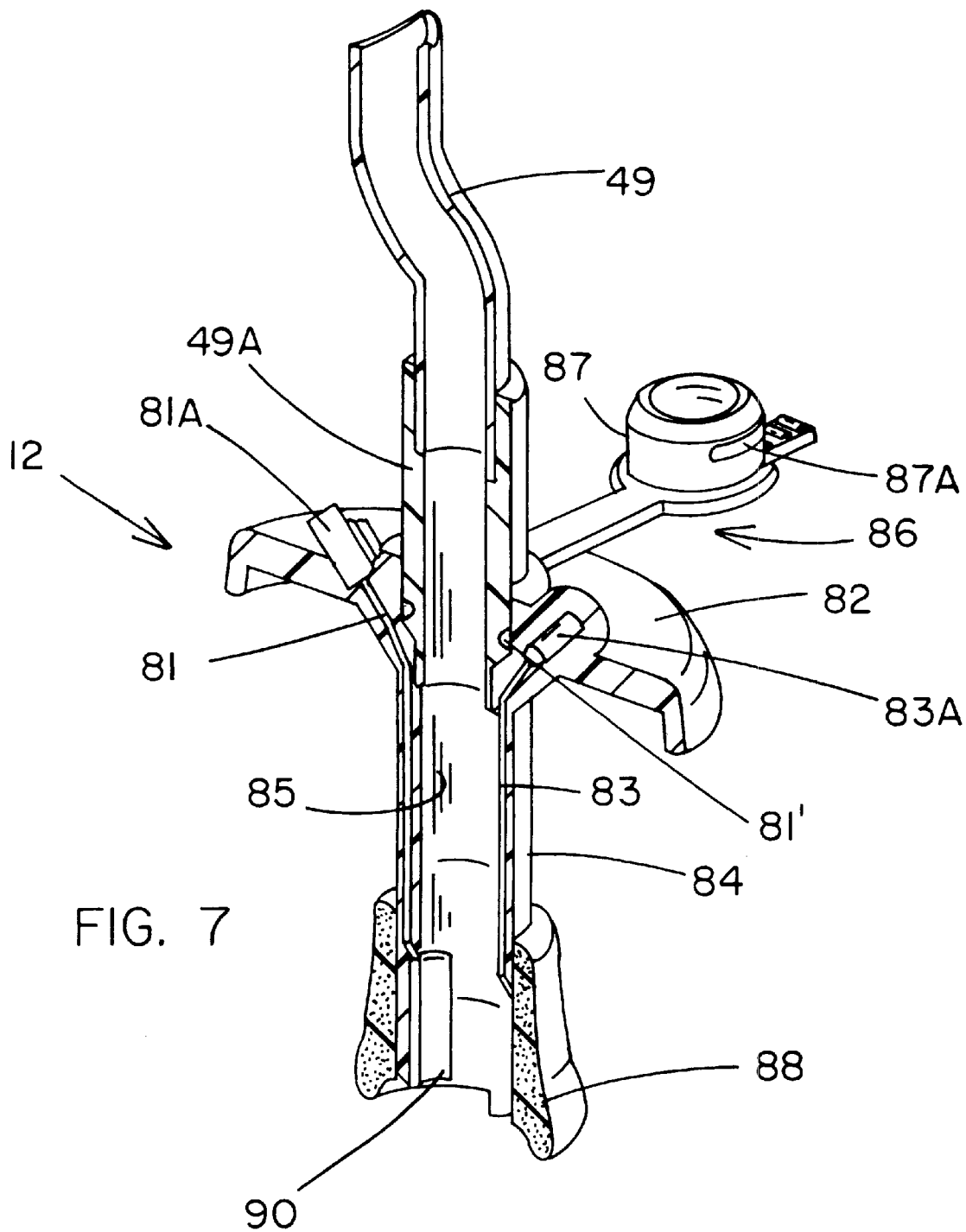
FIG. 7 is a longitudinal sectional view of the continent ostomy port of FIG. 5 with a drainage tube of the system in place for purging of the colon.

FIGS. 5A, 6 and 7 illustrate that the continent ostomy port ("COP") 12 previously mentioned is composed generally of a preferably low profile stomal disk or face plate 82 from one surface of which there extends a catheter portion, generally designated 84, for indwelling penetration of the stoma of a user, the "ostomate", and non-surgical insertion into the intestine, or other body organ which has been subjected to an ostomy procedure or a surgically created pouch/reservoir. The COP 12 and TOP 14 are described to some extent hereafter for better understanding of the use of new system 10.

A closure portion, generally designated 86, permits selective, openable covering of the distally disposed opening of the catheter through the stoma plate 82, and an internally disposed bolster or retention device, generally designated 88, maintains COP 12 in the necessary, implanted, operative position without the use of revisionary surgery or extraneous, externally applied materials such as belts, or adhesives. Bolster 88 may take a variety of forms, several embodiments of which have been described in the previously referred to application. All portions of COP 12 are formed of biocompatible materials, such as a sterilizable thermoplastic of known variety, such as polyurethane, for example.

Throughout this discussion the terms "proximal" and "distal" are used in the conventional medical manner; i.e., "distal" meaning farthest from the center of the body, and "proximal" being in the opposite direction, and are used in relation to the position of the claimed structure when new ostomy port 12 or various embodiments thereof are in operative position implanted in a stoma. Thus, "proximal" and "proximally disposed" are used in reference to the tip of a catheter 84, which is inserted into the stoma, and the terms "distal" and "distally disposed" are used to indicate the opposite end of the catheter, at which opposite end there is connected, transversely to the axis of the catheter 84, the stoma face plate 82.

COP 12, as shown in FIGS. 5A, 6 and 7 has paired detent grooves 87A formed on opposite sides of cap 87 to engage detent bars 81 ' and thereby retain closure portion 86 in a port closed position. Although the described closure structure is preferred, other useful closures can certainly be conceived which will suffice. For example, the detent mechanism can extend entirely around the neck and corresponding closure members. Alternatively, an annular groove can be formed around the inside wall at the distal end of catheter 84 at the distal end thereof and an annular ridge on neck cap portion correspondingly sized to snap-fit into the annular groove in secure, leak-free, detenting fashion. Further, the detent mechanism can be modified to use only one, or more than two sets of interacting, detenting bars and grooves. Regardless of the specific structure selected, this locking feature is important to the new system as later described.

Similarly, the shape and structure of closure portion 86 can be satisfactorily altered, although it is preferred that there be a mechanism provided to prevent inadvertent detachment and/or loss of the cap portion of the closure, so that the new continent ostomy port can always be selectively "closed". Of course, a cap member that is not tethered, or is removably tethered, as in FIG. 8, to the TOP (or COP) is still considered to be useful and in keeping with the invention.

Catheter member 84 is preferably generally tube-shaped and usually (although not necessarily) extends substantially perpendicularly to the plane of plate 82. However, catheter 84 is shaped and sized in diameter and length appropriately for the particular type of stoma for which the new port 12 is intended, it being understood that the new port is suitable and readily adapted for various types of ostomies and to any size of ostomate. Ordinarily the outside diameter of catheter member 84 will not be so large that port 12 cannot be gently, manually turned or "twirled" within its seat in the stoma. The continuous, inner side wall of catheter 84 defines a "major" lumen 85 and is most commonly straight and smooth to facilitate insertion and removal of a deodorizing cartridge or tampon and to deter accumulation of particles of waste.

In the example of new COP 12 shown in FIG. 6 there are formed longitudinally within the material of catheter 84, between walls one or more elongated air ducts or minor lumens, such as those indicated at 81, 83 for example. How many such lumen are provided the exact structure of which will vary depending upon the type of bolster provided on a particular COP, as well as with the type of anti-reflux valve ("ARV") used, if any.

Minor lumen 83 exits proximally through the exterior side wall of catheter 84, and can be in fluid communication with bolster portion 88. Whereas lumen 81 exits proximally through the interior side wall of catheter 84, to open into the larger, major lumen 85, and/or is operatively connected to an anti-reflux valve 90. The distal ends of the minor lumens both exit through plate 82, as illustrated, or in equivalent manner. The exterior access to lumen 83 is via a filtered "breather" port 83A, which provides a pressure relief mechanism for retention bolster 88. Exterior access to lumen 81 is via inflation/deflation valve 81 A, which provides a means of operating anti-reflux valve 90, for example by use of a syringe or any suitable conventional inflation/deflation device.

This feature is usually a repeatedly inflatable and deflatable cylindrical balloon structure that collapses upon deflation into a seat or depressed area of lumen 85 of catheter 84, preferably, but not necessarily at the extreme proximal end thereof, as shown. Anti-reflux valve 90 is in fluid communication with and is connected by lumen 81 to an inflation/deflation valve located on the outside or distal surface of stoma plate 82. When activated, or fully inflated, an ARV, such as 90, blocks the proximal opening of lumen to prevent inadvertent passage of intestinal contents from port. Typically, with the new COP, because of the presence of a deodorizing, filtration cartridge in lumen 84, the ARV 90 is in the non-activated, deflated position; inflation (activation) only being necessary during certain hygiene procedures, as explained below. Thus, contrary to ARVs conventionally used in long-term medical devices, the ARV of the new COP 12 is capable of much longer wear without material fatigue or other break-down.

In each case, the bolster 88 holds the COP in operative position by pressure placed by the bolster, radially from the longitudinal axis of catheter portion against the tissue of which the stoma is formed; e.g. the instestinal wall proximal to the stoma site. Thus, the internal tissue is gently pressed outwardly by the bolster in what is effectively an entirely internal "press-fit" or "friction fit" of the bolster against the tissue.

It is to be understood that the retention bolster styles of the new COP are referred to as "bioresponsive" because they perform the above-described reliable and secure site retention function without exerting damaging, excessive pressure against the surrounding tissue. It is necessary that the internal bolster does not dilate the bowel wall to such an extent that the vasculature is crimped or pinched. Excessive radial pressure to the lining of the bowel or other organ over any substantial period of time can cause ischema and/or bowel necrosis.

It is considered normal in non-ostomates for the bowel wall and any other hollow organ to become routinely squeezed at times, due to a spike in the pressure exerted by nearby, overlying or adjacent organs and/or musculature. In the case of an ostomate with an indwelling COP device, this may happen during exercise, heavy lifting, sexual activity or even by merely coughing. For example, when the stoma is pulled through a surgically created defect in the rectus abdominus muscles, any flexing of these muscles can cause a change in the internal pressure on the bowel wall. Accordingly, an internal retention bolster on a continent ostomy port, which is to be implanted for an extensive period of time, must be bioresponsive in order to accommodate such pressure changes by correspondingly adjusting its physical shape to maintain consistent sealing pressure, eliminating spikes in sealing pressure and thereby avoiding tissue damage. Although not absolutely required, the described bolster feature of the new COP is clearly a benefit for ostomates who wish to use new irrigation system 10, as such device 12 provides the secure closure needed for ambulation after irrigation fluid is introduced via system 10.

The bolster must be dynamic in nature, in order to routinely adjust by automatically collapsing and re-expanding, depending upon the needs and position of the bowel at a given time. Further, the new COP 12 generally; i.e. the plate and catheter portions may vary; i.e., in some views being schematically simplified, and not all elements will be shown in all views, which views are provided for illustrating the various forms of bolsters or other optional features and/or interchangeable features of the new COP. Regarding the various bolsters, it is to be further understood that the bolster portion, a preferred aspect of the new COP, is preferably, but not absolutely necessarily, bioresponsive. A retention bolster 88 which is formed as a spongy, foam-filled cuff or sleeve which entirely surrounds and is fixed to the cylindrical outer side wall of catheter, toward the proximal end thereof, spacedly from the position of face plate 82, so that there is comfortable room remaining, a matter of, for example, about three cm along the length of catheter 84 for receiving the surrounding stoma tissue. COP 12 can be made available in multiple sizes wherein this "free" length will vary typically between 2.5 and 7.0 cm to accommodate the differing thicknesses of users' abdominal walls.

The same detenting arrangement(s) (described above) used to keep cap 87 in closed position on COP 12 or TOP 14 (see FIG. 9) can also be used to selectively releasably lock an irrigation set 20 (FIG. 6) or a drainage tube 49 into use position. If desired, the distal port connection end of an irrigation or drainage tube set can also have, for example, formed detenting ridges or grooves, as however corresponds to the structure internally of whatever style of cap collar is in use in the particular port device selected.

FIGS. 8 and 9 show temporary ostomy port 14 in the open and closed positions, respectively. In FIG. 8 a drainage tube 49 is shown secured in place for selective evacuation of body waste. In FIG. 9 the drainage tube has been removed and TOP 14 is shown closed. Briefly, TOP 14 includes an elongated, substantially tubular body 89, an adjusting cone 95, a face plate 96 and a closure member 86 with a cap 87. The tubular body 89 and adjusting cone 95 interface with each other in such a manner as to provide longitudinal adjustability to accommodate variations in user's abdominal wall thickness and stoma height. Closure member 86 is optionally removable, for example, by releasable connection to a peg 86'. A stoma-locking "balloon" or bolster 92 which is preferably controlled by an inflation/deflation mechanism 94, is disposed on the proximal end of body 89 in order to selectively retain TOP 14 within the user's stoma. An anti-reflux valve (not shown) can also be included in TOP 14 to facilitate controlling inadvertent spillage of body fluids through TOP 14 upon insertion and removal of either the irrigation set 20 or drainage tube 49.

It is to be understood that the ports 12 and 14, as illustrated and described herein, are examples only and useful modifications of same will be apparent to those skilled in the art. For example, some structural features of ports 12 and 14 can conceivably be interchanged, or "borrowed", one from the other, and discussion of a structural feature with respect to only one the ports does not limit the scope of the invention to the port discussed always having such feature or the element to use in conjunction only with that particular style of port.

The provision of a closure portion on temporary ostomy port 14 may initially seem unnecessary, as the port is generally intended only for temporary placement in a stoma for drainage and irrigation. However, the closure member can be very useful, for example, if the user's bowel is somewhat impacted, it may be necessary to introduce water or other liquid into the bowl, via the port, and then close the port, to permit the user to move about for a period of time while the irrigation fluid acts within the bowel to soften and loosen the stool sufficiently to permit drainage. After a period of time the closure member can be opened, the drainage tube 49 introduced and locked in place within the stoma port and drainage can proceed. After completion of draining, the temporary port 14 can be removed and the user's ostomy bag, patch or plug attached to the stoma until the next time drainage is required.

FIG. 10 is a sectional view of an irrigation set 20 in normal use position, releasably "locked" by detenting engagement within the major lumen of temporary port 14. The internal connection of set 20 to TOP 14 is substantially the same as that of the drainage tube, and of the set 20 connected to COP 12.

FIG. 11 is a simplified, partial sectional view showing the distal portion of COP 12, enlarged and without the cap, in longitudinal section. An annular ridge or pawl protrudes slightly into lumen 84, just proximally of an internal shoulder. The ridge is palpably contacted by corresponding ridges on a variety of ostomy accessories. For example, detent ridges 56', 58' on an irrigation set connector 22 or a cone-tipped obturating device 58 respectively, such as those illustrated in FIGS. 12 and 13, will bump over the detent ridge as either of such devices are pushed into or pulled out of port 12 (or 14). The purpose of this feature is to provide the user with sufficient additional resistance to tactilely detect that the barrel 32 or other accessory (e.g., 22, 58), being removed is sufficiently far out of the major lumen of TOP 14 or COP 12 that the anti-reflux valve (not seen, but as in the COP of FIG. 7, for example) should be activated to prevent accidental release of body wastes.

Once the ARV in the TOP or COP is fully inflated the accessory in use can be completely removed from port 14, 12 and cleaned or discarded. Useful alternatives to the above-described structure include replacement of the pawl on an obturator or irrigation set connector nozzle with one or more slightly raised bumps or arcuate but non-annular ridges, so that less irregular surface area is present, which can trap fecal material within the lumen.

Use of the new ostomy irrigation system 10 is very simple and can be managed by the ostomate or a caregiver with very little training. The user ostomate has the benefit of the new continent ostomy port 12 or the temporary ostomy port 14 as a barrier to withhold all bowel contents (or other body fluid) until beginning of the drainage process is desired. Then, when drainage of fecal matter (or other body waste) is desired, the ostomate engages the anti-reflux valve of the COP or TOP to temporarily seal the proximally disposed (internal) end of the lumen of the port.

The closed ARV in ostomy port 12, 14 thereby prevents any inadvertent escape of fecal material into the port while the odor control cartridge is being removed and a drainage or irrigation device is being attached for the purpose of ostomy drainage and/or ostomy irrigation. Upon removal, the odor control cartridge is cleaned (if still functional) or discarded, at the discretion of the user. Alternatively, a conventional, non-flushable bag can be temporarily connected to the port, if necessary. Upon connection of the desired accessory, the user will simply deactivate the anti-reflux valve and purge the bowel of its contents. The purging process, as well as irrigation of the bowel, if preferred, can be done in the conventional manner, with the advantageous exception that once the irrigation tube 20 or purging (drainage) tube 49 is connected to the COP or TOP, the user's hands are free to attend to other tasks, such as shaving, make-up application, or otherwise, all while either the purging or irrigation process is carried on. Once drainage of the intestine is complete, and prior to removal of the accessory from the COP or TOP aperture, the ARV is again activated while a new or cleaned odor control cartridge is inserted. Then the anti-reflux valve is fully deactivated (opened) and the vented port cap (in the case of the continent ostomy port 12) is returned to the closed position, permitting the ostomate to go on about the business of daily life. In the case of a distal ostomy, after removal of the temporary irrigation port 14 an ostomy bag, plug or patch can be attached in the usual manner.

Thus, as has been shown, the new ostomy irrigation system provides savings in time by: (1) faster loosening of stool via pressurized pulsations of irrigant, (2) earlier stimulation of peristalsis by increasing irrigant exposure to a greater segment of bowel over a shorter period of time and by more rapid bowel excitation caused by pulsating jets of fluid impacting bowel wall, (3) hands-free use, allowing the ostomate to do other things while irrigating; and (4) facile portability of the entire system for ease of use at any location having basic toilet facilities. In addition, the user benefits from the lack of I.V. poles and gravity bags in the house, the small storage space required for and the portability of the entire system.

Moreover, the new system provides facile utilization due to: (1) lack of preparation required, quick setting of the time, temperature and pulse rate prior to use; (2) no filling of bags or trying to get around with an I.V. pole during infusion; (3) Preprogrammed temperature setting having the water ready at the desired level on arising in the morning; (4) irrigation port/stoma locking feature allowing hands-free irrigation; (5) adjustability of temporary ostomy port for comfort; (6) no re-heating of irrigating solutions required during infusion; (7) ability to disconnect and ambulate after infusion of fluids into the bowel; and (8) ready portability.

In view of the foregoing, it will be seen that the several objects of the invention are achieved and other advantages are attained. Although the foregoing includes a description of the best mode contemplated for carrying out the invention, various modifications are conceivable.

As various modifications could be made in the constructions and methods herein described and illustrated without departing from the scope of the invention it is intended that all matter contained in the foregoing description or shown in the accompanying drawings shall be interpreted as illustrative rather than limiting.

What is claimed is:

1. A port for temporary placement into an ostomy of a user, for use with an ostomy irrigation/drainage system, the port comprising: an adjusting cone to permit selective sizing to accommodate the anatomy of a user, and an elongated substantially tubular body having a first end and a second end, the first end being selectively releasably interconnectable to a tube connector set of the system and the second end being insertable into a stoma, to thereby permit controlled fluid introduction to or removal from the ostomy of the user, and further wherein the adjusting cone interfaces with the elongated tubular body, such that the port is longitudinally adjustable, to thereby permit selective sizing to accommodate the anatomy and stoma size of a particular user.

2. The port of claim 1, and further comprising a selectively operable retention member connected to the second end of the port, to thereby maintain the port in normal operative position in the ostomy until the irrigation or drainage procedure is complete and the port is intentionally removed.

3. The port of claim 1, and further comprising a closure member connectable to the first end of the substantially tubular body, to thereby permit the user to selectively ambulate for a period of time after introduction of fluid to the ostomy without spillage of irrigation fluid from the ostomy.

4. The port of claim 1, and further wherein the port is connectable to the skin of a user by an adhesive on a proximal side of the face plate of the port.

5. The port of claim 1, and further comprising an anti-reflux valve disposed within the second end of the port, to thereby prevent unintentional flow of fluids out of the port.

6. The combination of an ostomy port and a drainage tube, wherein the ostomy port comprises an elongated substantially tubular body having a first end and a second end, the first end being selectively releasably interconnectable to the drainage tube, and the second end being insertable into a stoma, to thereby permit controlled fluid removal from the ostomy of the user;

wherein the drainage tube comprises a first end and a second end, the first end having a detent mechanism thereon which is suitably sized and shaped to permit interlocking, substantially leak-proof detenting engagement with the ostomy port and the second end which is insertable into a receptacle for matter drained from the ostomy; and wherein the port is longitudinally adjustable, to thereby permit selective sizing to accommodate the anatomy and stoma size of a particular user.

7. The combination of an ostomy port and an ostomy bag, wherein the ostomy port comprises an elongated substantially tubular body having a first end and a second end, the first end being selectively releasably interconnectable with the ostomy bag and the second end being insertable into a stoma, to thereby permit controlled fluid removal from the ostomy of the user;

wherein the ostomy bag has an opening with a detent mechanism suitably shaped and sized to thereby permit substantially leak-proof, interlocking engagement with the ostomy port; and wherein the port is longitudinally adjustable, to thereby permit selective sizing to accommodate the anatomy and stoma size of a particular user.

8. The combination of an ostomy port and a gravity bag, wherein the ostomy port comprises an elongated substantially tubular body having a first end and a second end, the first end being selectively releasably interconnectable with the gravity bag and the second end being insertable into a stoma, to thereby permit controlled fluid introduction in the ostomy of the user;

wherein the gravity bag is adapted for substantially leak-proof, detenting, interlocking engagement with the ostomy port; and wherein the port is longitudinally adjustable, to thereby permit selective sizing to accommodate the anatomy and stoma size of a particular user.

9. The combination of claim 6, wherein the port further comprises a selectively operable retention member connected to the second end of the port, to thereby maintain the port in normal operative position in the ostomy until the irrigation or drainage procedure is complete and the port is intentionally removed.

10. The combination of claim 6, wherein the port further comprises a closure member connectable to the first end of the substantially tubular body, to thereby permit the user to selectively ambulate for a period of time after introduction of fluid to the ostomy without spillage of irrigation fluid from the ostomy.

11. The combination of claim 6, wherein the port is connectable to the skin of a user by an adhesive on a proximal side of the face plate of the port.

12. The combination of claim 6, wherein the port further comprises an anti-reflux valve disposed within the second end of the port, to thereby prevent unintentional flow of fluids out of the port.

13. The combination of claim 7, wherein the port further comprises a selectively operable retention member connected to the second end of the port, to thereby maintain the port in normal operative position in the ostomy until the irrigation or drainage procedure is complete and the port is intentionally removed.

14. The combination of claim 7, wherein the port further comprises a closure member connectable to the first end of the substantially tubular body, to thereby permit the user to selectively ambulate for a period of time after introduction of fluid to the ostomy without spillage of irrigation fluid from the ostomy.

15. The combination of claim 7, wherein the port is connectable to the skin of a user by an adhesive on a proximal side of the face plate of the port.

16. The combination of claim 7, wherein the port further comprises an anti-reflux valve disposed within the second end of the port, to thereby prevent unintentional flow of fluids out of the port.

17. The combination of claim 8, wherein the port further comprises a selectively operable retention member connected to the second end of the port, to thereby maintain the port in normal operative position in the ostomy until the irrigation or drainage procedure is complete and the port is intentionally removed.

18. The combination of claim 8, wherein the port further comprises a closure member connectable to the first end of the substantially tubular body, to thereby permit the user to selectively ambulate for a period of time after introduction of fluid to the ostomy without spillage of irrigation fluid from the ostomy.

19. The combination of claim 8, wherein the port is connectable to the skin of a user by an adhesive on a proximal side of the face plate of the port.

20. The combination of claim 8, wherein the port further comprises an anti-reflux valve disposed within the second end of the port, to thereby prevent unintentional flow of fluids out of the port.

* * * * *